(12) United States Patent
Bushong et al.

(10) Patent No.: US 10,113,187 B2
(45) Date of Patent: Oct. 30, 2018

(54) METHODS AND SYSTEMS FOR REDUCING ONE OR MORE IMPURITIES AND/OR MOISTURE FROM GRAIN OIL, AND RELATED COMPOSITIONS

(71) Applicant: Poet Research, Inc., Sioux Falls, SD (US)

(72) Inventors: David D. Bushong, Sioux Falls, SD (US); Casey C. Jenks, Tripp, SD (US)

(73) Assignee: Poet Research, Inc., Sioux Falls, SD (US)

(*) Notice: Subject to any disclaimer, the term of this patent is extended or adjusted under 35 U.S.C. 154(b) by 0 days.

(21) Appl. No.: 15/307,257

(22) PCT Filed: Apr. 27, 2015

(86) PCT No.: PCT/US2015/027792
§ 371 (c)(1),
(2) Date: Oct. 27, 2016

(87) PCT Pub. No.: WO2015/168020
PCT Pub. Date: Nov. 5, 2015

(65) Prior Publication Data
US 2017/0051322 A1    Feb. 23, 2017

Related U.S. Application Data

(60) Provisional application No. 61/985,197, filed on Apr. 28, 2014.

(51) Int. Cl.
| | | |
|---|---|---|
| *C12P 7/64* | (2006.01) | |
| *C12P 7/06* | (2006.01) | |
| *C12M 1/00* | (2006.01) | |
| *C11B 13/00* | (2006.01) | |
| *C11B 3/14* | (2006.01) | |

(52) U.S. Cl.
CPC ............... *C12P 7/64* (2013.01); *C11B 3/14* (2013.01); *C11B 13/00* (2013.01); *C12M 21/12* (2013.01); *C12M 47/10* (2013.01); *C12P 7/06* (2013.01); *Y02E 50/17* (2013.01); *Y02W 30/74* (2015.05)

(58) Field of Classification Search
CPC ........................................................ C12P 7/06
See application file for complete search history.

(56) References Cited

U.S. PATENT DOCUMENTS

| | | |
|---|---|---|
| 7,842,484 B2 | 11/2010 | Lewis |
| 7,867,365 B2 | 1/2011 | Brown |
| 7,919,291 B2 | 4/2011 | Lewis et al. |
| 7,960,574 B1 * | 6/2011 | Dickey ............... C11B 1/10 554/11 |
| 8,470,550 B2 | 6/2013 | Lewis |
| 8,497,082 B2 | 7/2013 | Lewis |
| 8,679,793 B2 | 3/2014 | Lewis |
| 8,702,819 B2 | 4/2014 | Bootsma |
| 9,061,987 B2 | 6/2015 | Bootsma |
| 2011/0086149 A1 | 4/2011 | Bootsma |
| 2012/0129234 A1 | 5/2012 | McDonald et al. |
| 2013/0109873 A1 | 5/2013 | Bootsma |
| 2013/0288376 A1 | 10/2013 | Lee |
| 2014/0053829 A1 | 2/2014 | Lee |
| 2014/0186907 A1 | 7/2014 | Bootsma |
| 2014/0242251 A1 | 8/2014 | Bootsma |
| 2015/0037857 A1 | 2/2015 | Redford |
| 2015/0197707 A1 | 7/2015 | Redford |
| 2015/0291923 A1 | 10/2015 | Bootsma |

FOREIGN PATENT DOCUMENTS

| | | |
|---|---|---|
| WO | 2013/126561 A1 | 8/2013 |
| WO | 2013/162966 A2 | 10/2013 |
| WO | 2017/059083 A1 | 4/2017 |

OTHER PUBLICATIONS

Minnesota, Minnesota Corn Growers Association Technical Symposium, 2001, pp. 1-7.*
International Search Report and Written Opinion from International Application No. PCT/US2015/27792, dated Oct. 19, 2015 (12 pages).

* cited by examiner

*Primary Examiner* — Bin Shen
(74) *Attorney, Agent, or Firm* — Kagan Binder, PLLC

(57) ABSTRACT

The present disclosure relates to methods and systems for injecting a gas (e.g., air) into a grain oil recovered from a grain process so as to remove an amount of one or more materials (e.g., moisture, unsaponifiables, insolubles, free fatty acids, and the like) from the grain oil.

14 Claims, 2 Drawing Sheets

METHODS AND SYSTEMS FOR REDUCING ONE OR MORE IMPURITIES AND/OR MOISTURE FROM GRAIN OIL, AND RELATED COMPOSITIONS

PRIORITY

This application claims benefit under 35 U.S.C. § 119(e) of U.S. Provisional Patent Application No. 61/985,197 filed Apr. 28, 2014 and titled "METHOD OF REDUCING IMPURITIES AND/OR WATER FROM AN OIL", wherein said provisional application is incorporated herein by reference in its entirety.

FIELD

The present disclosure relates to methods and systems for injecting a gas (e.g., air) into a grain oil recovered from a grain process so as to remove an amount of one or more materials (e.g., moisture, unsaponifiables, insolubles, free fatty acids, ethanol esters, and the like) from the grain oil.

BACKGROUND

In addition to the manufacture of alcohol from, e.g., carbohydrate materials of a feedstock, a number of co-products can be generated that are additional sources of revenue for the manufacturer. These co-products include, e.g., carbon dioxide gas for the industrial and food industries, protein rich animal feed products, and oils.

Corn oil is a common co-product from corn ethanol plants. Corn oil can be removed from the syrup co-product stream. Typical impurities in distiller's corn oil include moisture, insolubles, and unsaponifiables.

SUMMARY

Embodiments of the present disclosure include a method of making a grain oil product that includes:
  providing a grain material including:
  grain oil; and
  one or more oligosaccharides and/or one or more polysaccharides;
  converting at least a portion of the one or more oligosaccharides and/or one or more polysaccharides into one or more monosaccharides;
  fermenting at least a portion of the one or more monosaccharides to form a fermentation product including the grain oil and a biochemical;
  separating at least a portion of the grain oil from the fermentation product to form a grain oil product;
  providing at least a portion of the grain oil product into a vessel; and
  injecting a gas into the grain oil product in the vessel in a manner to form gaseous bubbles in the grain oil product and allow the gaseous bubbles to rise through at least a portion of the grain oil product within the vessel.

Embodiments of the present disclosure also include a method of making a grain oil product that includes:
  providing a grain material including:
  grain oil;
  grain solids; and
  one or more oligosaccharides and/or one or more polysaccharides;
  converting at least a portion of the one or more oligosaccharides and/or one or more polysaccharides into one or more monosaccharides;
  fermenting at least a portion of the one or more monosaccharides to form a fermentation product including the grain oil and a biochemical;
  distilling the fermentation product to remove at least a portion of the biochemical from the fermentation product and form a whole stillage composition, wherein the whole stillage includes the grain oil, the grain solids, and water;
  separating the whole stillage into cake and thin stillage;
  separating the thin stillage into syrup and a first grain oil product;
  providing at least a portion of the first grain oil product into a vessel; and
  injecting a gas into the first grain oil product in the vessel in a manner to form gaseous bubbles in the first grain oil product and allow the gaseous bubbles to rise through at least a portion of the first grain oil product within the vessel and form a second grain oil product.

Embodiments of the present disclosure also include a system for making a grain oil product that includes:
  a source of a grain material including:
  grain oil;
  grain solids; and
  one or more oligosaccharides and/or one or more polysaccharides;
  a first system configured to convert at least a portion of the one or more oligosaccharides and/or one or more polysaccharides into one or more monosaccharides, and ferment at least a portion of the one or more monosaccharides to form a fermentation product including the grain oil and a biochemical, wherein the first system is in fluid communication with the source of grain material;
  a second system configured to distill the fermentation product to remove at least a portion of the biochemical from the fermentation product and form a whole stillage composition, wherein the whole stillage includes the grain oil, the grain solids, and water, and wherein the second system is in fluid communication with the first system;
  a third system configured to separate the whole stillage into cake and thin stillage, wherein the third system is in fluid communication with the second system;
  a fourth system configured to separate the thin stillage into syrup and a first grain oil product, wherein the fourth system is in fluid communication with the third system; and
  a first vessel in fluid communication with the fourth system and a first source of gas, wherein the first vessel is configured to receive at least a portion of the first grain oil product into first vessel and inject the gas into the first grain oil product in the first vessel in a manner to form gaseous bubbles in the first grain oil product and allow the gaseous bubbles to rise through at least a portion of the first grain oil product within the first vessel and form a second grain oil product.

DETAILED DESCRIPTION

The present disclosure relates to refining a grain oil product that is recovered from a grain process. As described in detail below, the grain oil product can be refined by injecting gas into the grain oil product to remove one or more impurities such as moisture, unsaponifiables, insoluble, free fatty acids, and the like.

Figure 1A:
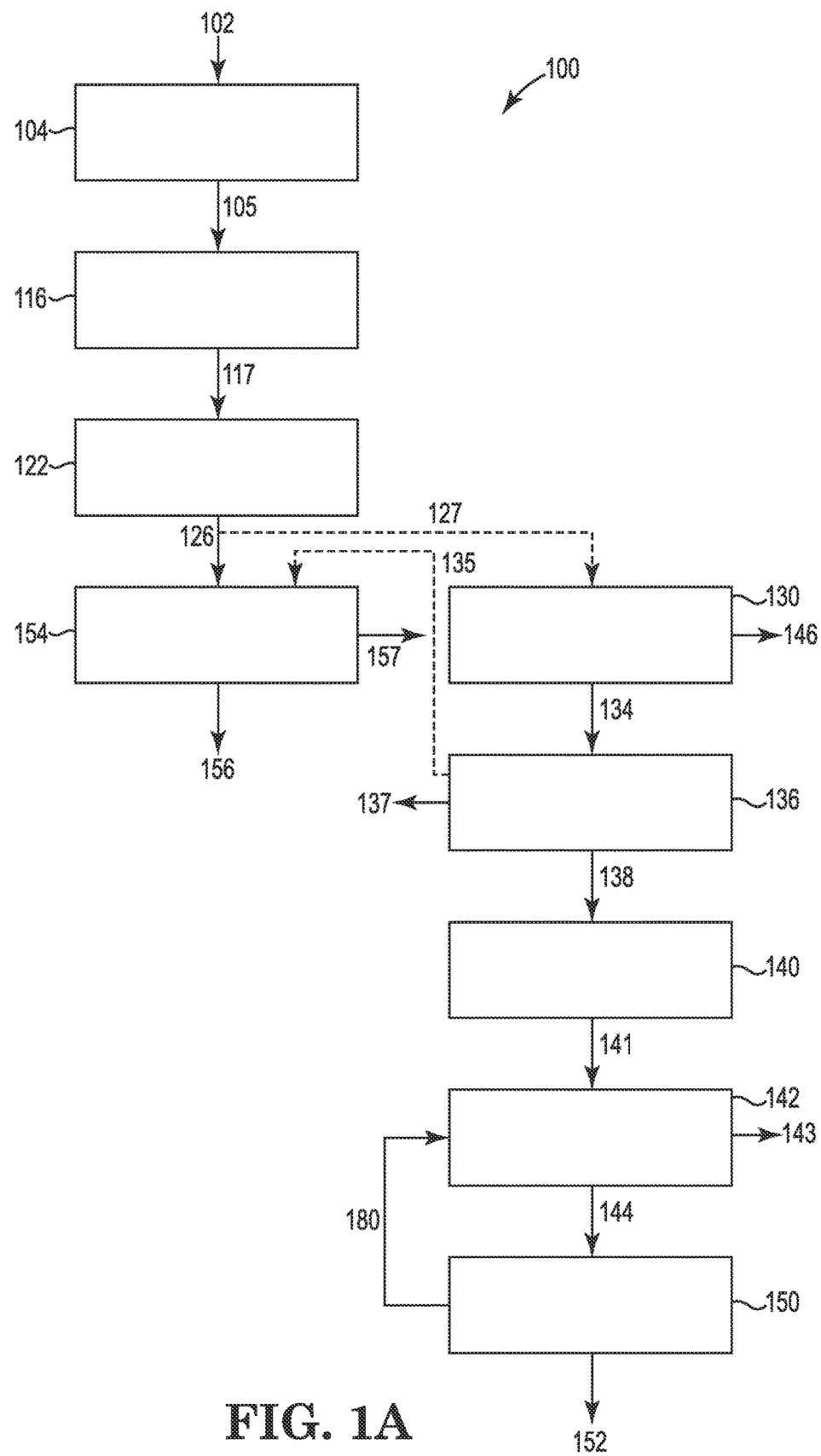
FIG. 1A shows an exemplary process flow diagram for removing one or more impurities from a corn oil product that is recovered from a corn ethanol production facility.
Figure 1B:
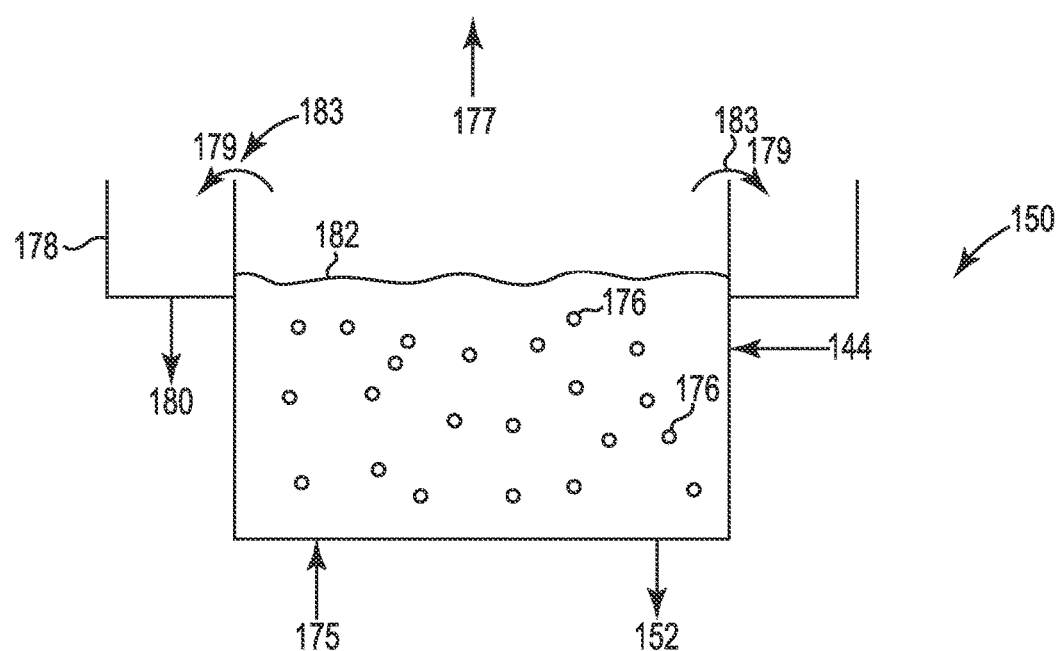
FIG. 1B shows a schematic of an exemplary vessel referred to in FIG. 1A for injecting gas into a corn oil product to remove one or more impurities from the corn oil product.

For illustration purposes, FIGS. 1A and 1B are discussed throughout below as an example of refining a corn oil product in the context of a dry milling corn ethanol facility. Methods of making corn oil from corn grain are also disclosed in WO 2013/126561 (Redford), U.S. Pub. No. 2015/0037857 (Redford), U.S. Pub. No. 2011/0086149 (Bootsma); U.S. Pub. No. 2013/0109873 (Bootsma); U.S. Pub. No. 2014/0186907(Bootsma); U.S. Pub. No. 2014/0242251 (Bootsma); and U.S. Pat. No. 8,702,819 (Bootsma), the entirety of each of said documents is incorporated herein by reference for all purposes.

Embodiments of the present disclosure can provide a source of grain material that can be processed to recover and refine an oil product. The grain material can include, for example, grain oil, grain solids, and one or more oligosaccharides and/or one or more polysaccharides.

Grain material can be provided from one or more grains such as corn, soybean, rapeseed, and the like.

The grain material can be prepared from a grain by a variety of techniques such as wet-milling (fractionation) or dry milling. For example, as shown in FIG. 1A whole corn 102 is delivered to preparation system 104 and can be dry-milled to generate grain material 105 (e.g., flour) suitable for fermentation. Alternatively, the corn 102 can be fractionated (wet-milled) using a fractionation system (not shown).

In wet-milling corn, for example, the corn bran (fiber) and germ components can be removed (sometimes referred to as a "full fractionation"), and the endosperm can be sent to the a milling system for size reduction to flour. Alternatively, only the fiber may be removed and the germ component and the endosperm component can be sent to a milling system for size reduction to flour (sometimes referred to as a "partial fractionation"). One benefit of dry-milling the entire corn kernel instead of fractionating is that the germ component includes starch and oil and the endosperm component includes starch and oil so overall ethanol production can be increased due to the higher level of starch and the overall oil production can be increased due to the higher level of oil.

The grain material can be processed to convert at least a portion of the polysaccharides and/or oligosaccharides into monosaccharides so that an organism (e.g., yeast) can use the monosaccharides to generate a biochemical. As shown in FIG. 1A, at least a portion of the one or more oligosaccharides and/or one or more polysaccharides can be converted into one or more monosaccharides in a system 116 (also called a saccharification system). For example, grain material such as milled corn 105 (or endosperm) can be slurried with water and one or more enzymes to liquefy the starch in milled corn and facilitate the conversion of starch into sugar (e.g. glucose). In many corn-to-ethanol facilities the flour slurry is typically heated in a jet cooker in order to convert the starch into sugar. However, by using an enzymatic approach, without any external heating to convert starch to sugar, relatively high temperatures involved in jet-cooking can be avoided. Jet-cooking temperatures can help generate impurities such as free-fatty acids, which as discussed below can be undesirable. Enzymatically converting polysaccharides and/or oligosaccharides to monosaccharides can occur at a temperature less than 180° F., less than 150° F., or even less than 120° F. Such an enzymatic process can benefit from a reduction in required energy, reduced overall costs, and minimal heat damage to the starch and proteins of the corn flour. Likewise, less heat damage occurs to the fats of the corn, thereby reducing the generation of free fatty acids. Enzymatically converting polysaccharides and/or oligosaccharides such as starch into monosaccharides is also described in U.S. Pat. No. 7,842,484 (Lewis), U.S. Pat. No. 7,919,291 (Lewis et al.), U.S. Pat. No. 8,470,550 (Lewis), U.S. Pat. No. 8,497,082 (Lewis), and U.S. Pat. No. 8,679,793(Lewis), the entirety of each of said documents is incorporated herein by reference for all purposes.

After generating the monosaccharides, the grain material including the grain solids, the grain oil, and the monosaccharides can be exposed to fermentation conditions to form a fermentation product including the grain oil, the grain solids, and a biochemical. As shown in FIG. 1A, the grain material 117 including one or more monosaccharides can be delivered from system 116 to the fermentation system 122, where at least a portion of the one or more monosaccharides can be fermented to form a fermentation product that includes at least the grain oil, grain solids, and a biochemical. Biochemicals that can be formed by fermenting monosaccharides include, for example, ethanol, butanol, and the like. For example, the sugar slurry from system 116 can be converted into ethanol by an ethanologen (e.g., yeast) in fermentation system 122. The product of fermentation (fermentation product) 126 can be a slurry referred to as "beer," which typically includes a liquid component, including ethanol, grain oil, water and soluble components, and a solids component, including unfermented particulate matter such as grain solids and the like.

Alternatively, saccharification system 116 and fermentation system 122 may be combined into a single system (not shown) referred to as simultaneous saccharification and fermentation (SSF) system.

After fermentation, the fermentation product (also referred to as "beer") can be distilled to remove at least a portion of the biochemical from the fermentation product and form a whole stillage composition. Whole stillage can include the grain oil, unfermentable solids such as grain solids, and water. As shown in FIG. 1A, the entire treated fermentation product (entire solid component and liquid component) 126 is fed directly to a distillation system 154. In the distillation system 154, the (treated) fermentation product is distilled to recover ethanol 156 and whole stillage 157, which includes water, soluble components, grain oil and unfermented solids (e.g., the solids component of the beer (e.g., unfermented grain solids) with substantially all ethanol removed). Distillation conditions can include temperatures of about 190° F. or higher. For example, 195° F. is a distillation temperature that can be used when operating under a vacuum. As another example, when operating under pressure, distillation temperatures can be from about 220-230° F.

The whole stillage can be separated into cake and thin stillage. Cake can include the majority of unfermentable solids present in the fermentation product, whereas thin stillage includes water, grain oil, fine unfermentable solids, unsaponifiables, and impurities such as free fatty acids. As shown in FIG. 1A, whole stillage 157 can be separated in system 130 into cake 146 and thin stillage 134. System 130 may include any solids separator such as a screw press, centrifugation system, filter/membrane system, and/or any other known solids separator unit.

Optionally, as indicated by dotted line 127, at least a portion of fermentation product 126 can be transferred directly to system 130 to separate the fermentation beer into a solids component and a liquid component.

The thin stillage can be separated into syrup and ultimately a first grain oil product 144. As shown in FIG. 1A, the thin stillage 134 is sent to system 136 to form syrup 137 and an oil in water emulsion 138. For example, although not shown in FIG. 1A, the thin stillage, which can have a solids content of about 10 percent or less can be concentrated to form an intermediate composition having a relatively increased solids content of about 15-25 percent. At least a portion of the intermediate composition can be centrifugally separated into an aqueous component (not shown) and an oil emulsion component 138. The remainder of the thin stillage can be further concentrated to have a higher solids content indicative of corn syrup 137 (e.g., greater than 25 percent solids). System 136 can include a concentrator such as a centrifugation system (such as a decanter centrifuge, disk stack centrifuge, and the like), an evaporation system, a filter/membrane system, and/or other known concentration techniques. For example, the thin stillage 134 may be put under pressure against a membrane with pores that enables the water and fines to pass through the membrane, and yet retain the larger oil or oil emulsion fraction. Optionally, if fermentation beer 127 is provided to system 130, the de-oiled liquids 135 (water and ethanol) can be provided to a distillation system 154 for the distillation of ethanol.

As shown in FIG. 1A, the oil emulsion component 138 can be de-emulsified in system 140. In some embodiments, the oil emulsion component 138 can be "broken" prior to oil separation. The de-emulsification may be performed by application of surfactant, electrical charge, or pH adjustment. System 140 may employ pH adjustment, electrostatic forces (i.e., passing the emulsion between two charged plates), physical shearing, surfactant addition, and other chemical treatments which change the surface properties of the emulsion. After the emulsion is disrupted, the composition 141 may be supplied to an oil separator 142 which generates a first oil product 144 and an aqueous phase 143 (also referred to as a "defatted emulsion"). Separator 142 may include a centrifuge system or a membrane based separation.

The first oil product 144 may have one or more impurities such as moisture, unsaponifiables, insolubles, free fatty acids, and the like. Unsaponifiables are a waxy type substance that are soluble in oil and can remain in the first oil product after de-emulsification. Insolubles can include fine solid material such as grain material (e.g., fiber and/or germ), starch, spent yeast cell material, and the like. Moisture, insolubles, and unsaponifiables can be referred to as "MIU" and can have specified limits for certain commercial applications. As shown in Table 1 below, a first oil product 144 may have average values that are within the specification limits, but because they can be so relatively close to the specification limits, they sometimes drift above the specification limits and are "out of spec." Such out of spec corn oil product can result in the corn oil being sold at a discount.

TABLE 1

Exemplary Specification and Average Values

| Parameter | Average Concentration Value | Specification Concentration Value |
| --- | --- | --- |
| Moisture | 0.56% | <0.6% |
| Insolubles | 0.115% | <0.4% |
| Unsaponifiables | 2.14% | <2.5% |
| Free Fatty Acids | 4.48% | <5% |
| MIU | 2.815% | <3.0% |

Embodiments of the present disclosure can reduce the level of one or more such impurities even further by passing a gas through the oil as described herein. For illustrations purposes, reference is made to system 150 in FIGS. 1A and 1B.

In more detail, embodiments of the present disclosure can inject a gas into the first grain oil product that is in vessel in a manner to form gaseous bubbles in the first grain oil product and allow the gaseous bubbles to rise through at least a portion of the first grain oil product within the vessel and form a second grain oil product. Passing a gas through the oil as described herein can also be referred to as "gas stripping" or "gas floatation" techniques. While not being bound by theory, it is believed that bubbles gaseous bubbles within the oil can permit a substance having relatively high vapor pressure (e.g., moisture) as compared to the bulk fluid (oil) to volatilize the moisture into the bubbles and be carried toward a top surface of the oil due to buoyancy of the bubble and exit the oil with the gas at the top surface of the oil. Also, while not being bound by theory, it is believed that fine insoluble particles can adhere to a surface of gaseous bubble and be carried toward a top surface of the oil due to buoyancy of the bubble and collect near the top surface of the oil. The insoluble particles can then be skimmed off the top of the oil.

An example of injecting gas into a first oil product as described herein is illustrated with first vessel 150 in FIG. 1B. As shown in FIG. 1B, first oil product 144 can be introduced relatively toward the top of first vessel 150 and a gas 175 can be injected into first vessel 150 so that the gas 175 and first oil product 144 operate in a counter current flow manner. Gaseous bubbles 176 can rise through first vessel 150 in the direction of 177 so as to remove one or more impurities from first oil product 144 and produce a second oil product 152 having reduced levels of one or more impurities. The gaseous bubbles 176 can exit the top surface 182 of the oil and the gas and vaporized impurities such as moisture can be carried away by any desired technique (e.g., venting to atmosphere, an exhaust fan/scrubber system, and the like). As shown in FIG. 1B, insoluble impurities that adhere to bubbles 176 can form a layer (e.g., foam layer) above the oil layer at interface 182. The foam 180 can overflow the top 183 of first vessel 150 as shown by arrows 179 and into weir 178. As shown in FIG. 1A, the foam (including insoluble particles) can be recycled to system 142 and ultimately be removed with aqueous phase 143.

First vessel can be any desired vessel suitable for removing impurities with gas as described herein. Exemplary first vessels include liquid only filled columns, packed towers (packed with ceramic and/or plastic pieces such as saddles), tray towers, and the like.

A gas can be chosen for bubbles 176 so as to facilitate mass transfer of moisture into the gas. Exemplary gases include air, carbon dioxide, inert gas such as nitrogen, and combinations thereof.

To facilitate injecting gas 176 into first oil product 144 the gas 176 can be compressed and the interior of first vessel 150 can operate at approximately atmospheric pressure. The compressed gas 175 can be selected to be higher that the head pressure of the oil in vessel 150 so that the desired gas flowrate can be injected into the vessel 150 and up through the oil. In some embodiments, the air can be dried with desiccant or other gas drying technology prior to being injected into first vessel 150 so as to be as dry as possible and facilitate transfer of moisture vapor from first oil product 144 into bubbles 176.

In some embodiments, compressed gas is injected into a vessel at a gas flow rate in the range from 0.1 to 5 ft$^3$/min/ft$^2$, or even from 0.25 to 2.5 ft$^3$/min/ft$^2$.

The first oil product 144 can be at a wide range of temperatures while gas is injected into it. While not being bound by theory, it is believed that in some embodiments relatively hot oil can help increase the vapor pressure of, e.g., moisture in the oil and facilitate mass transfer of the moisture from the oil into the gas bubbles. In some embodiments, the first oil product 144 in first vessel 150 can be a temperature in the range from 80° F. to 212° F., even 120° F. to 200° F.

Optionally, the second grain oil product 152 can be passed through a second vessel (not shown) in a manner as similarly described above with respect to first vessel 150. For example, a second vessel can include at least a portion of the second grain oil product and gas can be injected into the second grain oil product in a manner to form gaseous bubbles in the second grain oil product and allow the gaseous bubbles to rise through at least a portion of the second grain oil product within the second vessel and form a third grain oil product. Exemplary second vessels include liquid only filled columns, packed towers (packed with ceramic and/or plastic pieces such as saddles, rings, and the like), tray towers, and the like. In some embodiments, the second vessel can be a packed tower. While not being bound by theory, it is believed that a packed tower can be relatively more effective at removing moisture due to the increased contact between the liquid oil and gas caused by the packing.

Grain oil products refined according to the present disclosure can have desirably low levels of moisture and/or solids. In some embodiments, a grain oil product can include moisture in an amount in the range from greater than 0 to 0.3 percent by weight of the grain oil product, even in the range from greater than 0 to 0.25 percent by weight of the grain oil product.

In some embodiments, a grain oil product can include insoluble material in an amount in the range from greater than 0 to 0.1 percent by weight of the grain oil product, even in the range from greater than 0 to 0.05 percent by weight of the grain oil product.

In some embodiments, a grain oil product can include unsaponifiable material in an amount in the range from greater than 0 to 2.0 percent by weight of the grain oil product, even in the range from greater than 0 to 1.9 percent by weight of the grain oil product.

In some embodiments, a grain oil product can have an MN value in the range from greater than 0 to 3.0 percent by weight of the grain oil product, even in the range from greater than 0 to 2.5 percent by weight of the grain oil product.

Grain oil products (e.g., corn oil product) refined according to the present disclosure can have one or more applications such as an animal feed supplement, industrial uses, biodiesel production, and human grade edible oil, and the like.

EXAMPLE

Corn oil produced in accordance with an embodiment of the present disclosure yielded data as shown hi TABLE 2 below.

TABLE 2

|  | Initial | 5 Minute Sparge | 45 Minute Sparge |
| --- | --- | --- | --- |
| Moisture | 1.50% | 1.20% | 0.20% |
| Insolubles | 0.40% | 0.20% | 0% |
| Unsaponifiables | 2% | 2.10% | 1.80% |
| MIU | 3.90% | 3.50% | 2.00% |
| FFA | 3.50% | 3.00% | 2.10% |

What is claimed is:

1. A method of making a grain oil product comprising:
providing a grain material comprising:
grain oil;
grain solids; and
one or more oligosaccharides and/or one or more polysaccharides;
converting at least a portion of the one or more oligosaccharides and/or one or more polysaccharides into one or more monosaccharides;
fermenting at least a portion of the one or more monosaccharides to form a fermentation product comprising the grain oil and a biochemical;
distilling the fermentation product to remove at least a portion of the biochemical from the fermentation product and form a whole stillage composition, wherein the whole stillage comprises the grain oil, the grain solids, and water;
separating the whole stillage into cake and thin stillage;
separating the thin stillage into syrup and a first grain oil product, wherein separating the thin stillage into syrup and a first grain oil product comprises:
concentrating the thin stillage to form an intermediate composition;
centrifugally separating at least a first portion of the intermediate composition into an aqueous component and an oil emulsion component; and
de-emulsifying the oil emulsion component to form the first grain oil product
providing at least a portion of the first grain oil product into a vessel; and
injecting a gas into the first grain oil product in the vessel in a manner to form gaseous bubbles in the first grain oil product and allow the gaseous bubbles to rise through at least a portion of the first grain oil product within the vessel and form a second grain oil product.

2. The method of claim 1, wherein the gas is air, carbon dioxide, nitrogen, or combinations thereof.

3. The method of claim 1, wherein injecting comprises injecting compressed air into the vessel, wherein the vessel is at approximately atmospheric pressure.

4. The method of claim 3, wherein the compressed gas is injected at a gas flow rate in the range from 0.1 to 5 ft$^3$/min/ft$^2$.

5. The method of claim 1, wherein during at least a portion of the injecting the first grain oil product is at a temperature in the range from 120° F. to 200° F.

6. The method of claim 1, wherein the de-emulsifying comprises applying a shift in pH to the oil emulsion component.

7. The method of claim 1, further comprising:
providing the second grain oil product into a packed tower; and
injecting a gas into the second grain oil product in a manner to form gaseous bubbles in the second grain oil product and allow the gaseous bubbles to rise through at least a portion of the second grain oil product within the packed tower and form a third grain oil product, wherein the gas and second grain oil product pass through the packed tower in a counter current manner.

8. The method of claim 1, wherein the grain material comprises corn.

9. The method of claim 1, wherein providing a grain material comprises milling a plurality of corn kernels.

10. The method of claim 1, wherein the biochemical comprises ethanol.

11. The method of claim 1, wherein at least a portion of the converting occurs at a temperature below 180° F.

12. The method of claim 11, where the converting comprises exposing at least a portion of the one or more oligosaccharides and/or one or more polysaccharides to one or more enzymes to convert the one or more oligosaccharides and/or one or more polysaccharides into one or more monosaccharides.

13. A method of making a grain oil product comprising:
   providing a grain material comprising:
      grain oil;
      grain solids; and
      one or more oligosaccharides and/or one or more polysaccharides;
   converting at least a portion of the one or more oligosaccharides and/or one or more polysaccharides into one or more monosaccharides;
   fermenting at least a portion of the one or more monosaccharides to form a fermentation product comprising the grain oil and a biochemical;
   distilling the fermentation product to remove at least a portion of the biochemical from the fermentation product and form a whole stillage composition, wherein the whole stillage comprises the grain oil, the grain solids, and water;
   separating the whole stillage into cake and thin stillage;
   separating the thin stillage into syrup and a first grain oil product;
   providing at least a portion of the first grain oil product into a vessel; and
   injecting a gas into the first grain oil product in the vessel in a manner to form gaseous bubbles in the first grain oil product and allow the gaseous bubbles to rise through at least a portion of the first grain oil product within the vessel and form a second grain oil product, wherein injecting a gas into the first grain oil product forms a first layer comprising insoluble material and a second layer comprising the second grain oil product.

14. A method of making a grain oil product comprising:
   providing a grain material comprising:
      grain oil;
      grain solids, and
      one or more oligosaccharides and/or one or more polysaccharides;
   converting at least a portion of the one or more oligosaccharides and/or one or more polysaccharides into one or more monosaccharides;
   fermenting at least a portion of the one or more monosaccharides to form a fermentation product comprising the grain oil and a biochemical;
   distilling the fermentation product to remove at least a portion of the biochemical from the fermentation product and form a whole stillage composition, wherein the whole stillage comprises the grain oil, the grain solids, and water;
   separating the whole stillage into cake and thin stillage;
   separating the thin stillage into syrup and a first grain oil product;
   providing at least a portion of the first grain oil product into a vessel; and
   injecting a gas into the first grain oil product in the vessel in a manner to form gaseous bubbles in the first grain oil product and allow the gaseous bubbles to rise through at least a portion of the first grain oil product within the vessel and form a second grain oil product, wherein the gas and first grain oil product pass through the vessel in a counter current manner.

* * * * *